US005738827A

United States Patent [19]
Marquiss

[11] Patent Number: 5,738,827
[45] Date of Patent: Apr. 14, 1998

[54] APPARATUS FOR HOLDING REAGENT AND SAMPLE VESSELS

[75] Inventor: Samuel A. Marquiss, Santa Clara, Calif.

[73] Assignee: LJL Biosystems, Inc., Sunnyvale, Calif.

[21] Appl. No.: 518,564

[22] Filed: Aug. 23, 1995

[51] Int. Cl.⁶ .................................................. B01L 9/00
[52] U.S. Cl. ............................. 422/104; 422/58; 422/63; 422/64; 422/65; 422/102; 436/47; 206/564
[58] Field of Search ........................... 422/58, 61, 63, 422/64, 65, 72, 102, 104; 436/45, 47, 177, 809; 206/557, 558, 564, 521.6

[56] References Cited

U.S. PATENT DOCUMENTS

| | | | |
|---|---|---|---|
| 4,287,155 | 9/1981 | Tersteeg et al. | 422/64 |
| 4,849,177 | 7/1989 | Jordan | 422/64 |
| 4,900,513 | 2/1990 | Barker et al. | 422/64 |
| 4,961,906 | 10/1990 | Andersen et al. | 422/102 |
| 5,035,861 | 7/1991 | Grandone | 422/64 |
| 5,270,210 | 12/1993 | Weyrauch et al. | 436/43 |
| 5,456,882 | 10/1995 | Covain | 422/64 |

*Primary Examiner*—Harold Pyon
*Attorney, Agent, or Firm*—Lumen Intellectual Property Services

[57] ABSTRACT

An apparatus for holding reagent and sample vessels. The apparatus has reagent and sample vessel racks, a carousel supporting the racks, guiding pins that serve to guide the racks as they are mounted on the carousel and also serve to attach the racks to the carousel. Each of the racks has a handle that is used to lift the racks from the carousel. The grip of the handle is located above the center of gravity of its corresponding rack when the rack is lifted by the grip.

15 Claims, 4 Drawing Sheets

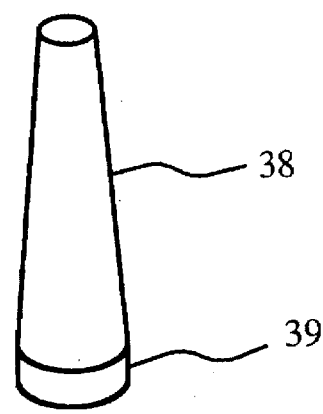
FIG. 3-A
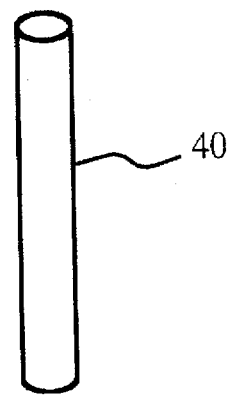
FIG. 3-B
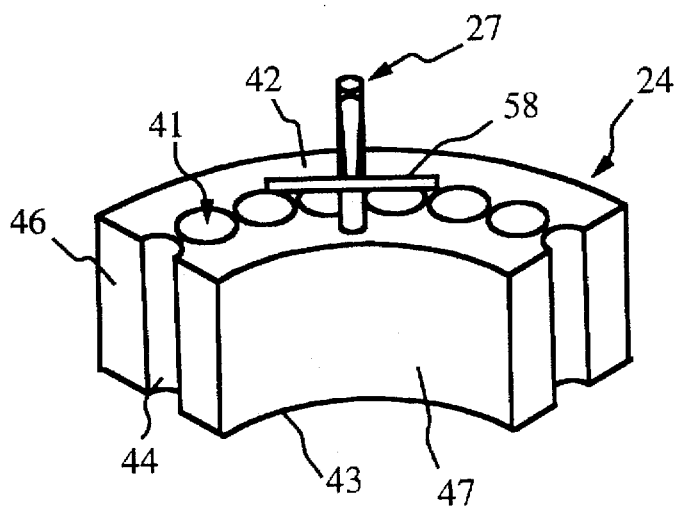
FIG. 4
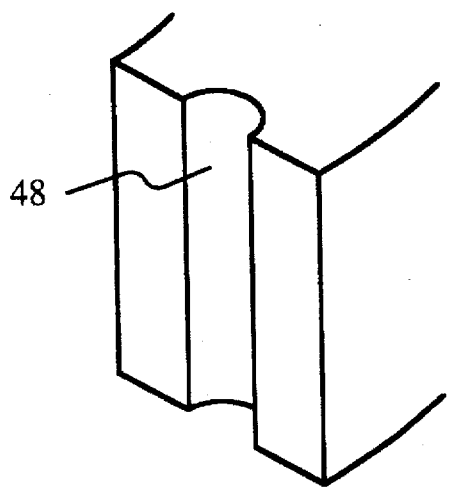
FIG. 5-A
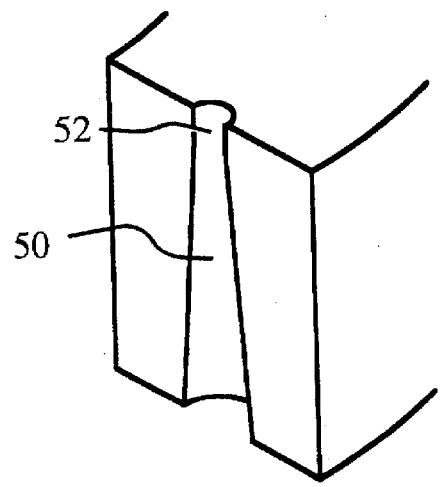
FIG. 5-B

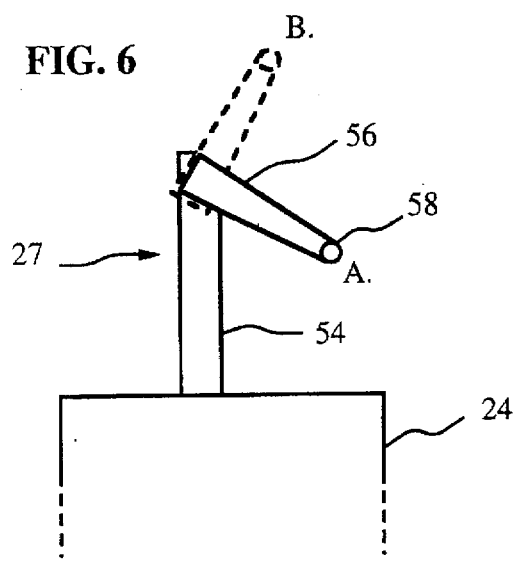
FIG. 6
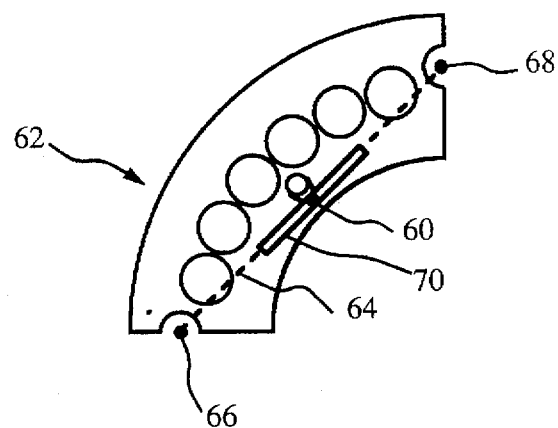
FIG. 7
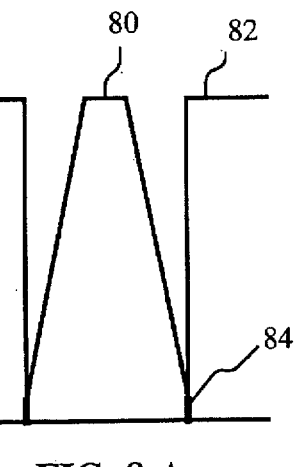
FIG. 8-A
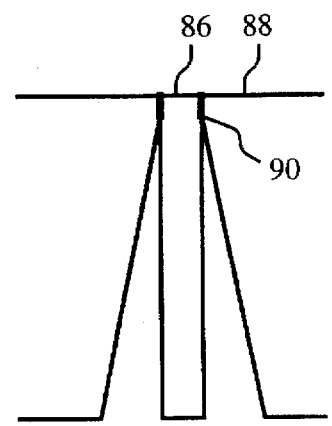
FIG. 8-B

APPARATUS FOR HOLDING REAGENT AND SAMPLE VESSELS

BACKGROUND—FIELD OF THE INVENTION

The present invention relates to the field of chemical analysis, and in particular to a vessel holder that comprises several racks for carrying reagent and sample vessels.

BACKGROUND—DESCRIPTION OF PRIOR ART

It is often useful in medical applications to run a given test on many similar samples. Such tests include the verification of the presence of substances or bacteria in blood or urine samples. An operator loads a number of sample and reagent vessels in an analyzer. The analyzer then automatically performs a given test on all the loaded samples.

The samples and reagents are placed on racks, which are mounted on a carousel. A mobile automatic arm can access sample and reagent vessels, and pipet liquid in and out of the vessels through an aspirate and dispense probe. Mounted on or next to the carousel are reaction cuvettes and a washing station for the aspirate and dispense probe. A small aliquot from a sample vessel is aspirated through the probe and dispensed to a reaction cuvette. The probe then successively aspirates reagents from reagent vessels and transfers each of the reagents to the reaction cuvette. Before dispensation, the reagents can be heated in a heater connected though tubing to the aspirate and dispense probe. After the sample-reagent mixture incubates for a period in the reaction cuvette, the reaction products are transferred to an analysis chamber and analyzed.

In many analyzers the sample and reagent vessels are placed on circular racks. For applications that require that the samples and reagents be stored at a set temperature (e.g. 37° C. for samples and 4° C. for reagents), it is useful to place the samples on racks made of a metal or some other thermally conducting material.

Once a given batch of samples has been analyzed, it is necessary to remove the sample vessels from the analyzer, and to load another batch onto the carousel. Also, it is often necessary to replace some of the reagent vessels. The ease of loading and unloading of the vessels is an important parameter in the design of an analyzer.

One design option is to semi-permanently attach the sample and reagent racks to the carousel. The vessels are then loaded and unloaded individually to and from the rack. Individual loading, however, can be time consuming for batches of many samples and/or reagents.

A way to reduce the dead time and to improve the ease of loading of the analyzer is to make the sample and reagent racks detachable from the carousel. When the analysis of a batch is finished, one can unload the sample rack and the reagent rack and replace them with new racks that had been loaded in advance with the appropriate vessels. Usually, a single rack is used for the samples, and a single one for the reagents. There are several disadvantages, however, to the typical approach of placing all the samples on a single sample rack and all the reagents on a single reagent rack.

For a typical sample rack holding 20–30 sample vessels, the size of the rack does not pose any handling problems. A sample rack containing 200 samples can be on the order of 1 meter in diameter, however, which is too large to allow easy handling. Also, a reagent rack holding 24 reagent vessels can weigh 12–13 pounds, assuming each reagent vessel holds about 250 cc of liquid. Often times only a fraction of the slots available on a rack are needed for a given batch. In such a case, the operator has to load and unload an unnecessarily large or heavy rack that is only partially full. Therefore the typical approach of designing a single holder for all the samples and reagents makes the loading and unloading of the samples and reagents inconvenient.

The ease of loading of the samples onto the analyzer also depends on the mechanism used to fasten the vessel racks to the carousel. The mechanism should allow for precise positioning and mechanical stability, as well as for easy loading of the racks onto the carousel.

Other prior art has been concerned mainly with improving the throughput of the analyzer by reducing the loading time. An example of such art is U.S. Pat. No. 4,849,177. Therein Jordan describes a rack system that allows the performance of multiple assays on a given set of samples. While Jordan's invention increases the throughput of the analyzer, it does not make loading easier or faster for a single-assay system.

OBJECTS AND ADVANTAGES OF THE INVENTION

It is a primary object of this invention to provide an easy-to-load, low cost vessel holder for a sample analyzer. This and other objects and advantages will become more apparent after consideration of the ensuing description and the accompanying drawings.

SUMMARY OF THE INVENTION

The objects and advantages of the invention are achieved with a vessel holder comprising a plurality of vessel racks. In particular, the vessel holder comprises a carousel, guiding pins mounted on the carousel, and vessel racks that can be mounted on the carousel. The vessel racks have wells for receiving reagent or sample vessels. The vessel racks also have grooves on some of their side walls. A fit is established between the guiding pins and the vessel racks along at least part of the grooves when the vessel racks are mounted on the carousel. Each of the vessel racks also has a handle. The grip of the handle is substantially above the center of gravity of the loaded vessel rack when the rack is lifted by the grip, so that the rack does not press on the guiding pins when it is lifted by the grip.

The essential aspect of the invention is that the vessel holder comprises more than one vessel rack, and that each vessel rack is attached to the carousel by simple and convenient means. This makes the loading and unloading of vessels significantly easier and faster than for other comparable systems.

BRIEF DESCRIPTION OF THE DRAWINGS

FIG. 3-A is a perspective view of a tapered guiding pin, according to the invention.

FIG. 3-B is a perspective view of a straight guiding pin, according to the invention.

FIG. 4 shows one of the vessel racks pictured in FIG. 1.

FIG. 5-A is a perspective view of a straight groove, according to the invention.

FIG. 5-B is a perspective view of a tapered groove, according to the invention.

FIG. 6 is a side view of a handle for lifting a vessel rack, according to the present invention.

FIG. 7 is a top view of a rack with a handle in a lifting position, according to the present invention.

FIG. 8-A shows the contact sections that ensure a clearance fit between a tapered pin and a straight-groove rack, according to the invention.

FIG. 8-B is a view similar to the one in FIG. 7-A, showing the fit between a straight pin and a tapered-groove rack.

DESCRIPTION

Figure 1:
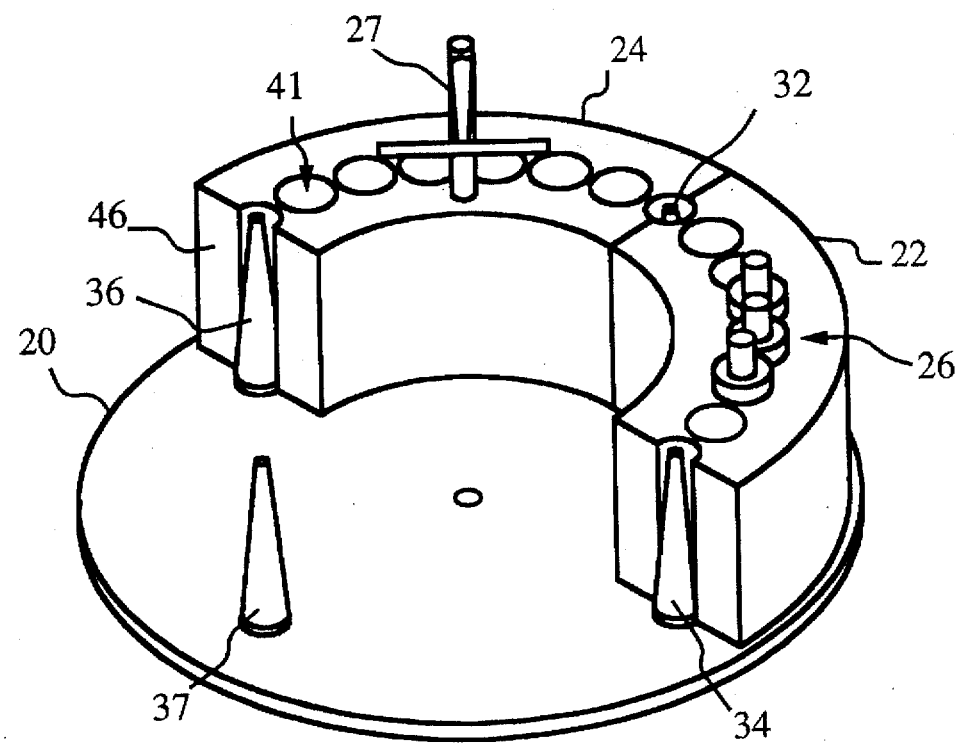
FIG. 1 is a perspective view of a carousel and two of the four vessel racks that can be mounted on the carousel, according to the invention.

FIG. 1 shows a carousel 20 and two vessel racks 22, 24. Two other vessel racks that can be mounted on carousel 20 are similar to racks 22, 24. Vessel racks 22, 24 hold vessels 26. A handle 27 is attached to rack 24; rack 22 has a handle similar to handle 27, not shown for clarity.

Figure 2:
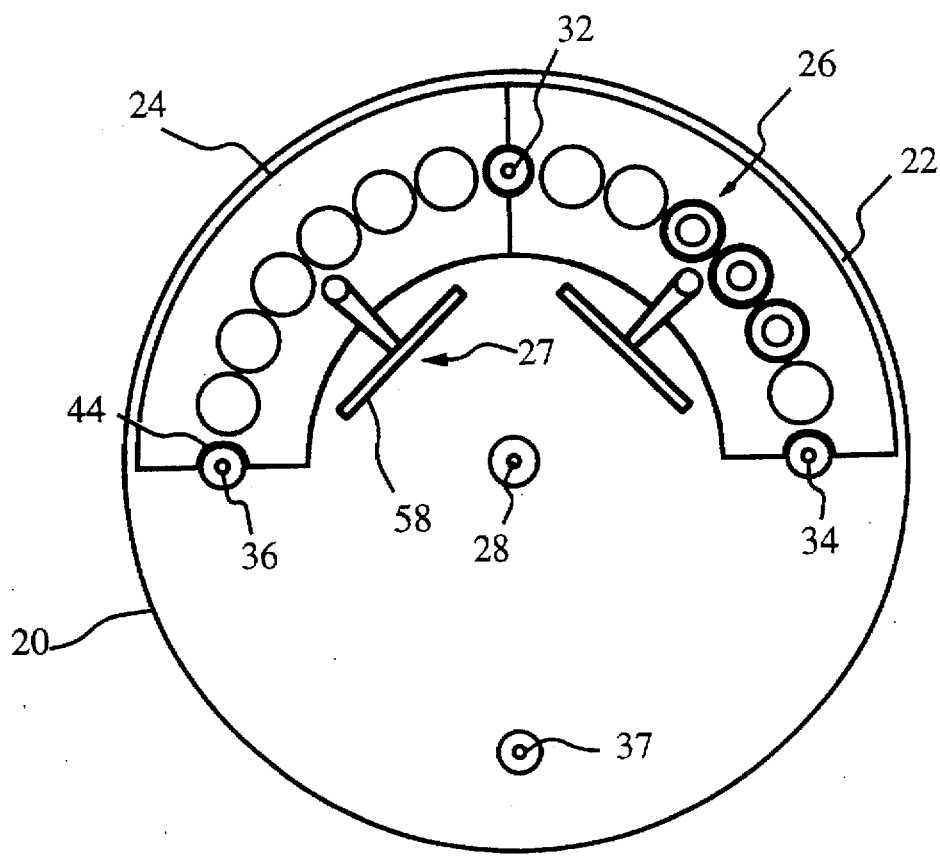
FIG. 2 is a top view of the apparatus shown in FIG. 1.

FIG. 2 is a top view of the arrangement shown in FIG. 1. Carousel 20 can rotate around an axis of rotation 28. The rotation of carousel 20 around axis 28 is used to position successive vessels 26 under a mobile arm equipped with an aspirate and dispense probe (not shown). The guiding pins 32, 34, 36, 37 are attached to carousel 20, and serve to secure racks 22, 24 onto carousel 20. Two possible guiding pin shapes are shown in FIG. 3-A and 3-B: FIG. 3-A shows a tapered pin 38, while FIG. 3-B shows a straight pin 40. Tapered pin 38 has a straight section 39, along which the fit between pin 38 and its corresponding racks takes place.

FIG. 4 is a perspective view of rack 24. Rack 24 has an arcuate shape; it has a top side 42, a bottom side 43, and side walls, two of which are labeled in the figure: the walls 46 and 47. Rack 24 also has several wells 41 for receiving vessels. The openings of wells 41 are arranged on top side 42. Bottom side 43 rests on a carousel (not shown). Rack 24 also has a groove 44 in side wall 46; there is a similar groove 45 in the side wall opposite wall 46. The grooves can be straight or tapered; FIG. 5-A and 5-B show, respectively, a straight groove 48 and a tapered groove 50. Tapered groove 50 has a straight section 52 along which the fit between the rack and its adjacent pin takes place.

Rack 24 can be lifted by handle 27. FIG. 6 is a longitudinal sectional view of handle 27. Handle 27 has a fixed part 54, a swivelable part 56 and a grip 58. Swivelable part 56 can move between a resting position A and a lifting position B. When swivelable part 56 is in lifting position B, grip 58 is approximately above the center of gravity of the rack, so that there is no net torque on rack 24 when rack 24 is lifted by grip 58. Preferably, the position of the center of gravity of rack 24 does not depend on whether rack 24 is or is not loaded with vessels 26. The placement of grip 58 above the center of gravity of rack 24 ensures that rack 24 does not press on its corresponding guiding pins as it is lifted vertically by grip 58. However, since the liquid levels in vessels 26 may vary, the position of the center of gravity of the rack loaded with vessels may also vary. Therefore, it is desirable to make rack 24 heavy enough so that small variations in the liquid level in vessels 26 lead to minimal changes in the position of the center of gravity of rack 24.

Preferably, the grooves of a rack of this invention are placed such that their longitudinal axes and a vertical axis passing through the center of gravity of the rack are coplanar. Such an arrangement is shown in FIG. 7. The center of gravity 60 of the rack 62 is situated substantially on a horizontal line 64 intersecting the longitudinal axes 66 and 68 of the rack grooves. The torque on rack 62 due to pin-groove contact can be non-zero if the grip of handle 70 is not precisely above the center of gravity of rack 62. A placement of grooves 66 and 68 as described above minimizes the torque on rack 62 due to pin-groove contact as rack 62 is lifted by its handle 70. Handle 70 is shown in FIG. 7 in its lifting position, similar to the position B shown in FIG. 6.

A clearance fit can be established between a tapered pin 80 and a straight-groove rack 82, as shown in a longitudinal sectional view in FIG. 8-A, or between a straight pin 86 and a tapered-groove rack 88, as shown in FIG. 8-B. The contact between guiding pin 80 and vessel rack 82 takes place near the bottom of rack 82, along the straight section 84 of pin 80. The contact between guiding pin 86 and vessel rack 88 takes place near the top of vessel rack 88, along the straight section 90 of the groove of vessel rack 88, as shown in FIG. 8-B.

Referring back to FIG. 2, tapered pin 32 is in contact with vessel racks 22, 24 when vessel racks 22, 24 are mounted on carousel 20. Rack 24 slides between pins 32 and 36; as rack 24 reaches the surface of the carousel, the portion of groove 44 near the bottom side of rack 22 is in close proximity to the straight section of pin 36. The attachment of tapered-groove racks to straight pins occurs in a manner similar to the one described above.

Figure 9:
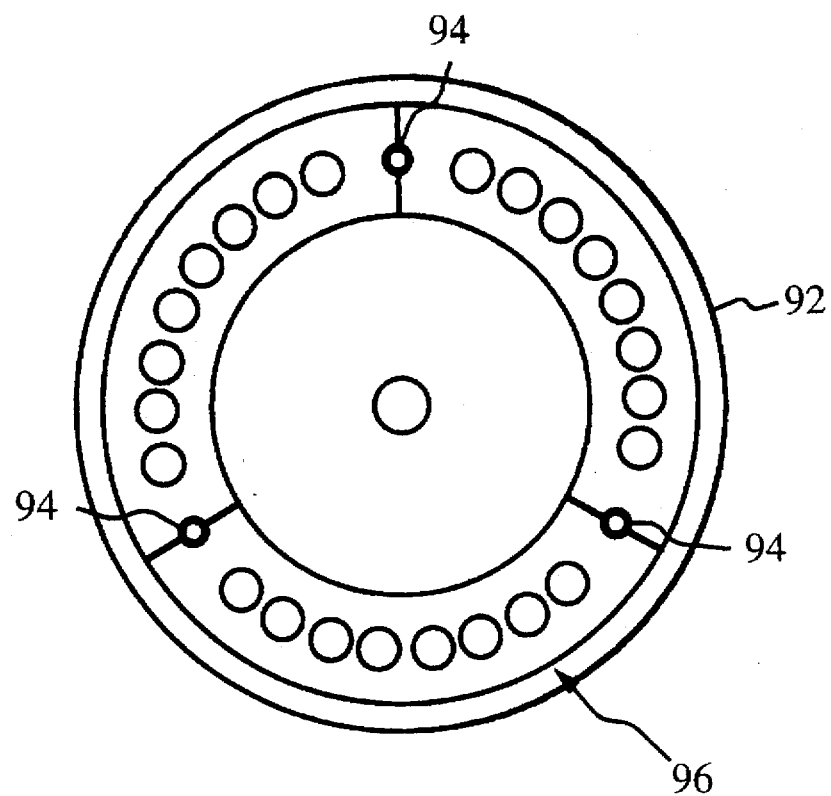
FIG. 9 is a top view of an arrangement of three identical vessel racks on a carousel.
Figure 10:
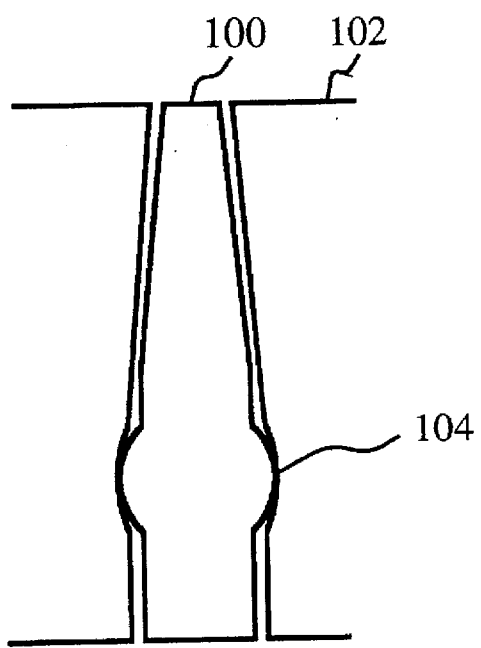
FIG. 10 is a sectional view of a tapered pin and a straight-groove rack in a snap fit.

An embodiment similar to the one described above is pictured in FIG. 9. FIG. 9 shows a carousel 92 with three guiding pins 94. Carousel 92 can support three vessel racks 96. One can envision alternative methods of securing the vessel racks to the guiding pins. FIG. 10 is a sectional view of a guiding pin 100 and of rack grooves that would be suitable for the attachment of the rack 102 to pins similar to pin 100 by a snap fit. The fit takes place along a contact section 104 of pin 100.

SUMMARY, RAMIFICATIONS, AND SCOPE

A new design for a vessel holding apparatus has been described. The apparatus includes several racks that can be easily loaded onto a carousel. The racks are attached to the carousel by a press fit to a number of guiding pins mounted on the carousel. The modular nature of the apparatus, as well as the simple rack loading mechanism, help reduce the time required for the loading and unloading of vessels onto/from the carousel.

It is clear that many modifications can be made to the above apparatus, without departing from the spirit of the invention. For example, the shape of the racks need not necessarily be arcuate. Many fitting mechanisms can be used to attach the racks to the guiding pins. A handle having no moving parts can be used to lift each rack. Moreover, a base plate can be used to support the racks; the base plate may be a fixed plate or a carousel, for example. Therefore, the scope of the invention should be determined not by the examples given, but by the appended claims and their legal equivalents.

I claim:

1. An apparatus for holding vessels comprising:
   a) a base plate;
   b) a plurality of tapered guiding pins mounted vertically on said base plate, the bottoms of said tapered guiding pins resting on said base plate, the width of said tapered guiding pins being largest at said bottoms of said tapered guiding pins;

c) a plurality of vessel racks, each of said vessel racks having a top side, a bottom side, side walls, and a plurality of wells for receiving vessels, each of said wells having an opening in said top side, each of said vessel racks having a plurality of grooves running vertically along at least a pair of said side walls opposite each other, such that said grooves guide said vessel racks as said vessel racks slide down along said tapered guiding pins, and such that a fit is established between said vessel racks and said tapered guiding pins along at least a section of said tapered guiding pins when said vessel racks have completed a downward sliding motion along said tapered guiding pins; and d) a handle comprising a fixed part attached to said top side, a swivelable part attached to said fixed part, and a grip attached to said swivelable part, said swivelable part being able to swivel between a resting position and a lifting position; wherein said grip is substantially above the center of gravity of said vessel rack when said swivelable part is in said lifting position; and wherein said center of gravity is situated substantially on a horizontal line intersecting the longitudinal axes of at least two of said grooves.

2. The apparatus of claim 1 wherein said fit is a snap fit.

3. The apparatus of claim 1 wherein said grip is substantially above the center of gravity of said vessel rack when said vessel rack is lifted by said grip.

4. The apparatus of claim 3 wherein said center of gravity is situated substantially on a horizontal line intersecting the longitudinal axes of at least two of said grooves.

5. The apparatus of claim 1 wherein each of said vessel racks has an arcuate shape.

6. The apparatus of claim 5 wherein said openings of said wells are arranged substantially along said vessel racks, such that when all said vessel racks are mounted on said base plate, said openings are arranged in a circle.

7. The apparatus of claim 1 wherein said fit is a clearance fit.

8. An apparatus for holding vessels comprising:

a) a base plate;

b) a plurality of straight guiding pins mounted vertically on said base plate;

c) a plurality of vessel racks, each of said vessel racks having a top side, a bottom side, side walls, and a plurality of wells for receiving vessels, each of said wells having an opening in said top side, each of said vessel racks having a plurality of tapered grooves running vertically along at least a pair of said side walls opposite each other, the depth of said tapered grooves being largest at said bottom side, such that said tapered grooves guide said vessel racks as said vessel racks slide down along said straight guiding pins, and such that a fit is established between said vessel racks and said straight guiding pins along at least a section of said straight guiding pins when said vessel racks have completed a downward sliding motion along said straight guiding pins;

d) a handle comprising a fixed part attached to said top side, a swivelable part attached to said fixed part, and a grip attached to said swivelable part, said swivelable part being able to swivel between a resting position and a lifting position; wherein said grip is substantially above the center of gravity of said vessel rack when said swivelable part is in said lifting position; and wherein said center of gravity is situated substantially on a horizontal line intersecting the longitudinal axes of at least two of said grooves.

9. The apparatus of claim 8 wherein said fit is a snap fit.

10. The apparatus of claim 8 wherein said fit is a clearance fit.

11. The apparatus of claim 8 wherein said grip is substantially above the center of gravity of said vessel rack when said vessel rack is lifted by said grip.

12. The apparatus of claim 11 wherein said center of gravity is situated substantially on a horizontal line intersecting the longitudinal axes of at least two of said grooves.

13. The apparatus of claim 8 wherein each of said vessel racks has an arcuate shape.

14. The apparatus of claim 13 wherein said openings of said wells are arranged substantially along said vessel racks, such that when all said vessel racks are mounted on said base plate, said openings are arranged in a circle.

15. An apparatus for holding vessels comprising:

a) a base plate;

b) a plurality of guiding pins mounted vertically on said base plate;

c) a vessel rack having side walls and a plurality of grooves running vertically along at least a pair of said side walls opposite each other, such that said grooves guide said vessel racks as said vessel racks slide down along said guiding pins; and d) a handle comprising a fixed part attached to said vessel rack, a swivelable part attached to said fixed part, and a grip attached to said swivelable part, said swivelable part being able to swivel between a resting position and a lifting position; wherein said grip is substantially above the center of gravity of said vessel rack when said swivelable part is in said lifting position; and said center of gravity is situated substantially on a horizontal line intersecting the longitudinal axes of at least two of said grooves.

* * * * *